(12) United States Patent
Heese et al.

(10) Patent No.: US 12,168,146 B2
(45) Date of Patent: Dec. 17, 2024

(54) SYSTEM, METHOD AND COMPUTER PROGRAM FOR DETERMINING A RADIATION THERAPY PLAN FOR A RADIATION THERAPY SYSTEM

(71) Applicant: Elekta Inc., Atlanta, GA (US)

(72) Inventors: Harald Sepp Heese, Hamburg (DE); Torbjoern Vik, Hamburg (DE); Rolf Jürgen Weese, Norderstedt (DE)

(73) Assignee: Elekta Inc., Atlanta, GA (US)

( * ) Notice: Subject to any disclaimer, the term of this patent is extended or adjusted under 35 U.S.C. 154(b) by 170 days.

(21) Appl. No.: 17/780,507

(22) PCT Filed: Nov. 25, 2020

(86) PCT No.: PCT/EP2020/083266
§ 371 (c)(1),
(2) Date: May 26, 2022

(87) PCT Pub. No.: WO2021/110495
PCT Pub. Date: Jun. 10, 2021

(65) Prior Publication Data
US 2023/0001236 A1     Jan. 5, 2023

(30) Foreign Application Priority Data
Dec. 2, 2019 (EP) ..................................... 19212897

(51) Int. Cl.
*A61N 5/10* (2006.01)

(52) U.S. Cl.
CPC ......... *A61N 5/1036* (2013.01); *A61N 5/1031* (2013.01); *A61N 5/1045* (2013.01)

(58) Field of Classification Search
CPC ... A61N 5/1036; A61N 5/1031; A61N 5/1045
See application file for complete search history.

(56) References Cited

U.S. PATENT DOCUMENTS

| 2010/0054413 A1 | 3/2010 | Sobering |
| 2013/0121469 A1 | 5/2013 | Sobering |

(Continued)

FOREIGN PATENT DOCUMENTS

| EP | 3831448 A1 | 6/2021 |
| WO | WO2018141606 A1 | 8/2018 |
| WO | WO-2021110495 A1 | 6/2021 |

OTHER PUBLICATIONS

Yan et al., "A fast optimization approach for treatment planning of volumetric modulated arc therapy", Radiation Oncology, vol. 13, No. 101, 13 pages. (Year: 2018).*

(Continued)

*Primary Examiner* — Kiho Kim
(74) *Attorney, Agent, or Firm* — Schwegman Lundberg & Woessner, P.A.

(57) ABSTRACT

The invention relates to a system for determining a radiation therapy plan for a radiation therapy system (100), comprising a multi-leaf collimator. The radiation therapy plan determination system (110) comprises a therapy system characteristics providing unit (111), wherein the characteristics comprise possible leaf positions and possible radiation fluence values, a planning objectives providing unit (112), wherein the planning objectives are indicative of a desired therapeutic radiation dose distribution, an optimization function providing unit (113), wherein the optimization function is indicative of a deviation of a radiation dose distribution from the planning objectives and of an uncertainty of the radiation dose distribution at edges of the possible apertures, and a therapy plan optimization unit (114) adapted to determine a sequence of possible apertures and possible radiation fluence values for which the optimization function is optimized. Thus, an optimal therapy plan can be provided for each individual patient.

20 Claims, 4 Drawing Sheets

(56) References Cited

U.S. PATENT DOCUMENTS

2016/0082287 A1    3/2016    Isola
2018/0078786 A1    3/2018    Vik
2019/0209863 A1    7/2019    Ollila

OTHER PUBLICATIONS

PCT International Search Report, International application No. PCT/EP2020/083266, Jan. 19, 2021.

Younge K. C. et al., "Penalization of Aperture Complexity in Inversely Planned Volumetric Modulated Arc Therapy", Medical Physics, AIP, Melville, NY, US, vol. 39, No. 11, Nov. 1, 2012, pp. 7160-7170, XP012160745.

Unkelbach J. et al., "Accounting for Range Uncertainties in the Optimization of Intensity Modulated Proton Therapy", Physics in Medicine and Biology, vol. 52, pp. 2755-2773, 2007.

Zygmanski P. et al., "Dependence of Fluence Errors in Dynamic IMRT on Leaf-Positional Errors Varying with Time and Leaf Number", American Association of Physics Medecine, vol. 30, No. 10, pp. 2736-2749, Oct. 2003.

Park J. M. et al., "The Effect of MLC Speed and Acceleration on the Plan Delivery Accuracy of VMAT", British Institute of Radiology, vol. 88, No. 1049, p. 20140698, 2015.

Webb S. et al., "Some Considerations Concerning Volume-Modulated Arc Therapy: A Stepping Stone Towards a General Theory", Physics in Medicine & Biology, vol. 54, No. 14, pp. 4345-4360, Jul. 2009.

Feygelman V. et al., "Initial Dosimetric Evaluation of SmartArc—A Novel VMAT Treatment Planning Module Implemented in a Multi-Vendor Delivery Chain", Journal of Applied Clinical Medical Physics, vol. 11, No. 1, 2010.

Hårdemark A. et al. "Pinnacle3® White Paper: P3IMRT® Direct machine parameter optimization", 2004 http://incenter.medical.philips.com/doclib/enc/5162119/P3IMRT_-_Direct_machine_parameter_optimization.pdf%3Ffunc%3Ddoc.Fetch%26nodeid%3D5162119%26vernum%3D3.

"European Application Serial No. 19212897.3, Extended European Search Report mailed Apr. 17, 2020", 9 pgs.

"European Application Serial No. 19212897.3, Invitation to remedy deficiencies (R. 58 EPC) mailed Feb. 3, 2020", 3 pgs.

"European Application Serial No. 19212897.3, Response filed Mar. 5, 2020 to Invitation to remedy deficiencies (R. 58 EPC) mailed Feb. 3, 2020", 33 pgs.

"International Application Serial No. PCT/EP2020/083266, International Preliminary Report on Patentability mailed Jun. 16, 2022", 9 pgs.

"International Application Serial No. PCT/EP2020/083266, Written Opinion mailed Jan. 19, 2021", 7 pgs.

\* cited by examiner

SYSTEM, METHOD AND COMPUTER PROGRAM FOR DETERMINING A RADIATION THERAPY PLAN FOR A RADIATION THERAPY SYSTEM

CROSS-REFERENCE TO RELATED APPLICATIONS

This patent application claims the priority benefit under 35 U.S.C. § 371 of International Patent Application no. PCT/EP2020/083266, filed Nov. 25, 2020, which claims the benefit of European Patent Application No. EP19212897.3, filed on Dec. 2, 2019. These applications are hereby incorporated by reference herein in their entirety.

FIELD OF THE INVENTION

The invention relates to a system, a method and a computer program for determining a radiation therapy plan for a radiation therapy system, comprising a multi-leaf collimator (MLC).

BACKGROUND OF THE INVENTION

Today, for radiation therapy, often radiation systems are used that comprise a multi-leaf collimator (MLC). MLCs comprise a plurality of movable leaves and allow to adapt the radiation beam provided by the radiation therapy system to the individual shape and structure of a therapy region, for instance, of a tumor that should be radiated. To optimize the radiation dose distribution received by a patient during a radiation therapy, therapy plan optimization algorithms are used to optimally adapt a therapy plan, i.e. a sequence of positions of the leaves of the MLC and of fluence values that can be provided by the radiation therapy system, to an individual patient. However, in many cases the same radiation dose distributions can be achieved with different therapy plans, i.e. with different sequences of leaf positions and fluence values. In these cases, a radiologist decides, based on his/her experience, which therapy plan, i.e. which sequence of leaf positions and fluence values, should be used for an individual patient. However, this decision process does not always lead to the most optimal therapy plan for a patient.

SUMMARY OF THE INVENTION

It is an object of the present invention to provide a system, a method and a computer program that allow to improve the determination of a therapy plan such that an optimal therapy plan can be provided for each individual patient.

In a first aspect of the invention a radiation therapy plan determination system is presented, wherein the radiation therapy plan determination system is adapted to determine a radiation therapy plan for a radiation therapy system comprising a multi-leaf collimator (MLC), wherein the MLC comprises a plurality of moveable leaves for shaping an aperture of the MLC such that a radiation beam is shaped by the aperture before being provided to a patient, wherein the radiation therapy plan determination system comprises a) a therapy system characteristics providing unit for providing characteristics of the radiation therapy system, wherein the characteristics comprise possible leaf positions defining possible apertures of the MLC and possible radiation fluence values that are providable by the radiation therapy system, b) a planning objectives providing unit for providing planning objectives, wherein the planning objectives are indicative of a desired therapeutic radiation dose distribution that should be provided to the patient, c) an optimization function providing unit for providing an optimization function being indicative of a deviation of a radiation dose distribution from the planning objectives, wherein the radiation dose distribution depends on a sequence of possible apertures defined by the possible leaf positions and possible radiation fluence values, and wherein the optimization function is further indicative of an uncertainty of the radiation dose distribution at edges of the possible apertures, d) a therapy plan optimization unit for determining an optimized therapy plan, wherein the therapy plan optimization unit is adapted to determine a sequence of possible apertures and possible radiation fluence values for which the optimization function is optimized, wherein the sequence of optimized possible apertures and optimized possible fluence values defines the optimized therapy plan.

Since the optimization function is indicative of an uncertainty of the radiation dose distribution at edges of possible apertures, uncertainties in the radiation dose distribution provided by the radiation therapy system caused, for instance, by scattered radiation or positioning inaccuracies at the edges of the apertures of the MLC, can be taken into account directly as part of the optimization process. Thus, a therapy plan can be determined that is not only optimized with respect to a desired dose distribution but also provides as little uncertainty of the provided dose distribution as possible. Since the uncertainty is a measure of possible deviations from an optimal therapy plan, i.e. radiation dose distribution, a low uncertainty in the radiation therapy plan ensures that the radiation dose distribution provided to the patient very accurately follows the determined radiation therapy plan. Thus, the therapy plan determination is improved such that a more optimal therapy plan can be provided for each individual patient.

The radiation therapy plan determination system is adapted to determine a radiation therapy plan for a radiation therapy system. The radiation therapy system can be any kind of system that is used in a radiation therapy in which radiation should be provided to a part of the patient, for instance, to a tumor. The provided radiation can be any kind of ionizing radiation used in medical therapies. Preferably, the radiation therapy system provides therapeutic x-ray radiation to a patient. Alternatively, the radiation therapy system can be adapted to provide protons during a proton radiation therapy to a patient.

The radiation therapy system comprises an MLC, wherein the MLC provides a plurality of movable leaves that can be used for shaping an aperture of the MLC. Radiation provided by the radiation therapy system is then shaped by the aperture before being provided to the patient. In an embodiment, the leaves of the MLC are provided as leaf pairs that are arranged at each side of an axis in a plane formed by the leaves of the MLC. However, other arrangements of leaves of the MLC can also be contemplated.

The therapy system characteristic providing unit is adapted to provide characteristics of the therapy system. The therapy system characteristics providing unit can be a storing unit in which the characteristics of a therapy system are stored already and from which the characteristics can be retrieved, for instance, based on a list containing characteristics for a plurality of radiation therapy systems. Also, the therapy system characteristics providing unit can be a retrieving unit for retrieving the characteristics from, for instance, a radiation therapy system for which a radiation therapy plan should be determined, wherein the therapy systems characteristics providing unit is then adapted to provide the received characteristics.

The provided characteristics refer to characteristics of the radiation therapy system that have an influence on the radiation dose distribution provided to the patient. In particular, the characteristics comprise possible leaf positions defining possible apertures of the MLC and possible radiation fluence values that are providable by the radiation therapy system. The possible leaf positions refer to the positions of the leaves of the MLC of the radiation therapy system that can be adopted by the leaves, due to the construction of the MLC of the radiation therapy system. For instance, the possible leaf position can be provided as position coordinates for each leaf determining the positions that a respective leaf can adopt in accordance with the construction of the MLC. The possible radiation fluence values refer to the fluence values that can be provided by the radiation therapy system. For instance, the possible radiation fluence values can refer to one or more x-ray radiation fluence values that the radiation therapy system can provide due to its construction. In an embodiment, the radiation therapy system can be adapted to provide only one radiation fluence value, i.e. to provide only a constant amount of radiation, wherein in this case the therapy system characteristics providing unit is adapted to provide the one possible radiation fluence value as part of the characteristics of the therapy system.

The planning objectives providing unit is adapted to provide planning objectives. The planning objectives providing unit can be a storing unit in which the planning objectives are already stored and from which the planning objectives can be retrieved. Also, the planning objectives providing unit can be a retrieving unit for retrieving the planning objectives from, for instance, an input device into which a user inputs the planning objectives, wherein the planning objectives providing unit is then adapted to provide the received planning objectives.

The planning objectives refer to objectives that should be reached by the radiation therapy for an individual patient. In particular, the planning objectives are indicative of a desired therapeutic radiation dose distribution that should be provided to the patient. For instance, the planning objectives can specify regions in a patient that should receive a high radiation dose or regions in a patient that should, if possible, only receive a low radiation dose, or even regions that should not receive any radiation at all. The planning objectives, for instance, the regions that should receive the different radiation doses, can be determined, for instance, by a radiologist based on previously acquired images of the region of interest of a patient. For instance, a radiologist can determine and select a tumor region in which a high radiation dose should be received, a region of surrounding tissue that should, if possible, only receive a low radiation dose, and a region comprising a radiation sensitive organ that should not receive any radiation at all. These planning objectives are then indicative for the desired therapeutic radiation dose distribution. However, in other embodiments a user, like a radiologist, can directly provide a desired radiation dose distribution as planning objective to the planning objectives providing unit, for instance, via an input unit.

The optimization function providing unit is adapted to optimize an optimization function. The optimization function providing unit can be a storing unit in which the optimization function is already stored and from which the optimization function can be retrieved. For instance, the storing unit can comprise different optimization functions, wherein the optimization function providing unit is adapted to select an optimization function, for example, based on the characteristics of the radiation therapy system. Also, the optimization function providing unit can be a retrieving unit for retrieving the optimization function from, for instance, an input unit which can be used by a user to select an optimization function, wherein the optimization function providing unit is then adapted to provide the received optimization function. The optimization function is indicative of a deviation of a radiation dose distribution from the planning objectives. For instance, the optimization function can provide a difference between an arbitrary radiation dose distribution and the planning objectives, for example, by indicating regions in which the planning objectives are not met for the radiation dose distribution. In an embodiment, the optimization function can be directly calculated as a difference between a radiation dose distribution and a desired therapeutic radiation dose distribution that is provided as part of the planning objectives or determined based on the information given by the planning objectives.

The radiation dose distribution depends on a sequence of possible apertures defined by the possible positions and possible radiation fluence values. A sequence of possible apertures and possible radiation fluence values can be defined by at least one possible aperture and at least one possible fluence value, but can also refer to a plurality of possible apertures and possible radiation fluence values that should be provided to the patient in a chronological order during the radiation therapy. Preferably, all possible apertures of a sequence are associated with one possible fluence value. In other embodiments, in a sequence of possible apertures, each possible aperture of the sequence can also be associated with more than one fluence value. Each possible aperture associated with one or more possible radiation fluence values defines a radiation dose distribution such that a sequence of possible apertures and possible radiation fluence values defines a sequence of partial radiation dose distributions, wherein a sum of all radiation dose distributions defines the radiation dose distribution received by the patient when the radiation therapy system provides the radiation according to the sequence.

The optimization function is further indicative of an uncertainty of the radiation dose distribution at edges of the possible apertures. The uncertainty at the edges of the possible apertures can, for instance, be caused by radiation scatter at these edges or due to positioning inaccuracies of the leaf defining the aperture. The uncertainties in the position of the edges of a possible aperture of the MLC directly lead to uncertainties in a radiation dose distribution defined by the possible aperture. This uncertainty of the radiation dose distribution can be modeled for one or more edges, preferably, for all edges, of the possible aperture. The optimization function is then adapted such that it takes these uncertainties of the radiation dose distribution into account. Preferably, the optimization function depends on these uncertainties.

The therapy plan optimization unit is adapted to determine an optimized therapy plan, wherein the optimized therapy plan is defined by a sequence of optimized possible apertures and optimized possible fluence values. To determine the optimized therapy plan, the therapy plan optimization unit is adapted to determine a sequence of possible apertures and possible radiation fluence values for which the optimization function is optimized. In particular, the optimization function is optimized if the deviation between the radiation dose distribution and the planning objectives becomes small, for instance, as small as possible. Based on the mathematical definition of the optimization function the minimizing of the deviation can refer to a minimizing or maximizing of the optimization function, i.e. to determining a local or global extremum of the optimization function. For instance, the therapy plan optimization unit can be adapted to use iterative methods, like the method of gradient descent, or direct methods, like direct machine parameter optimization, for finding the optimized therapy plan. Moreover, the therapy plan optimization unit can be adapted to use a two step optimization method for optimizing the optimization function, wherein in a first step a fluence distribution is optimized and in a second step the optimized fluence distribution is converted into a sequence of possible apertures, i.e. into possible leaf positions, and radiation fluence values. Alternatively, the therapy plan optimization unit can be adapted to optimize the optimization function in one step, for instance, by using direct machine parameter optimization algorithms in which the sequence of apertures and radiation fluence values, i.e. the machine parameters, are optimized at the same time. In this case a nonlinear optimization method can be used that can handle, for instance, nonlinear constrains, to optimize the optimization function with respect to the objectives. Such a method is preferably used if the radiation therapy should be provided in a step-and-shoot protocol or in a volumetric modulated arc therapy protocol. Alternatively, the therapy plan optimization unit can also be adapted to use a column generation approach.

Since the optimization function is indicative of the uncertainties of the radiation dose distribution at edges of possible apertures defining the radiation dose distribution, this uncertainty of the radiation dose distribution is also taken into account during the determination of the sequence of possible apertures and possible radiation fluence values for which the optimization function is optimized, i.e. the optimized therapy plan, is also optimized with respect to these uncertainties.

In an embodiment, the uncertainty of the radiation dose distribution is determined based on the possible leaf positions of the MLC defining the possible apertures and based on the possible radiation fluence values on which the radiation dose distribution depends. Since the possible leaf positions define the possible apertures and thus also the edges of the possible apertures, the uncertainty of a radiation dose distribution defined by a sequence of possible apertures can be determined very accurately based on the possible leaf positions defining the possible apertures. Moreover, in a preferred embodiment the radiation dose distribution is determined based on the positions of the tips of the leaves defining the possible aperture. For instance, if the MLC comprises leaf pairs arranged along an axis of the MLC, the tips of each leaf define edges of the aperture that are parallel to the axis of the MLC, i.e. edges in the movement direction of the leafs of the MLC. Alternatively or additionally, the uncertainty of the radiation dose distribution can also be determined based on the edges between neighboring leaves, wherein the leaf positions of the neighboring leaves define the length of the edge between neighboring leaves. In particular, the edges between neighboring leaves of MLCs comprising leaf pairs arranged around an axis of the MLC define edges of the aperture perpendicular to the axis of the MLC, i.e. perpendicular to the movement direction of the leafs of the MLC. Moreover, it is also preferred that radiation fluence values associated with a possible aperture are also taken into account for determining the uncertainty of the radiation dose distribution. For instance, the uncertainty of a radiation dose distribution defined by a possible aperture can be regarded as being proportional to the radiation fluence value associated with the possible aperture.

In a preferred embodiment, the uncertainty of a radiation dose distribution defined by a sequence of possible apertures and possible fluence values is determined based on the uncertainties of each partial radiation dose distribution defined by each possible aperture associated with a possible fluence value being part of the sequence defining the radiation dose distribution. For instance, an uncertainty can be modeled for each partial radiation dose distribution and then it can be summed over all uncertainties of all partial radiation dose distributions contributing to the radiation dose distribution.

In an embodiment, the therapy plan optimization unit is adapted to determine the sequence of possible apertures and possible fluence values for which the optimization function is optimized such that a sequence of possible apertures and possible fluence values is preferred as optimized therapy plan that leads to a radiation dose distribution with less uncertainty. Preferably, the optimized therapy plan is determined such that the uncertainty of a radiation dose distribution defined by the determined optimized therapy plan is less than an uncertainty of a radiation dose distribution defined by another therapy plan, wherein both radiation dose distributions are the same. For instance, if during the optimization two therapy plans are found that provide the same optimal radiation dose distribution to the patient, but comprise different sequences of possible apertures and possible fluence values, the optimization function is optimized such that from these two plans the plan providing less uncertainty to the radiation dose distribution is chosen as optimized therapy plan. In an embodiment, the optimization function can be optimized such that the uncertainty of the radiation dose distribution of the optimized therapy plan is as small as possible. In an embodiment, a weight is predetermined and provided in the optimization function for the uncertainty of the radiation dose distribution such that therapy plans with less uncertainty comprise a higher weight during the optimization of the optimization function than therapy plans with a higher uncertainty. Additionally or alternatively, the therapy plan optimization unit can be adapted to determine the sequence of possible apertures and possible fluence values for which the optimization function is optimized such that a sequence of possible apertures and possible fluence values is preferred as optimized therapy plan that lead to a homogenous uncertainty of the radiation dose distributions. A homogenous uncertainty refers to an uncertainty distribution without an accumulation of uncertainty at distinct points. For instance, the uncertainty can be regarded as being homogenous if the variance of the uncertainty lies beneath a predetermined threshold, wherein the variance V can be determined, for instance, by using the mathematical term $V=\int(U(x)-avg(U(x)))^2 dx$, wherein U is the uncertainty. Alternatively, the uncertainty can be regarded as being homogenous if the term $\int U(x)^2 dx$ is below a predetermined threshold. The threshold can be determined depending on the expected uncertainty distribution, or based on general theoretical or experimental data with respect to which inhomogeneity of the uncertainty is acceptable for a specific radiation therapy. In an embodiment, the uncertainty for a radiation dose distribution is modelled based on an uncertainty function centered at at least one edge of each possible aperture, wherein the uncertainty function of an edge comprises a width corresponding to an anticipated uncertainty for the respective edge. The uncertainty function can be any kind of function that is suitable for modeling the uncertainty of the radiation dose distribution caused by the edges of the possible apertures defining the radiation dose distribution. In a preferred embodiment, the uncertainty function refers to a Gaussian type function. However, the uncertainty function can also refer to another probability function, for instance, an accordingly scaled and normalized basis function of a cubic spline or an asymmetric function like a Gamma distribution.

The uncertainty function comprises a width that corresponds to an anticipated uncertainty for a respective edge around which the uncertainty is centered. The anticipated uncertainty can be determined, for instance, based on known construction margins of the MLC, scatter characteristics of the leaves of the MLC, calibration measurements performed for the MLC, positioning accuracy of the leaves of the MLC, etc. For determining the width, for instance, a standardized phantom might be used and subjected to a radiation therapy plan, wherein a difference between a simulated dose and the measured dose for this radiation therapy plan can be determined for different leaf positions. Based on these measurements a width of an uncertainty for a respective edge of a given MLC can be determined.

In a preferred embodiment, the uncertainty function of each edge is weighted with a possible fluence value that is associated with the possible aperture to which the edge belongs. Weighting the uncertainty function of each edge based on the possible fluence value associated with the edge, i.e. the possible aperture to which the edge belongs, allows to take into account a dependency of the uncertainty from the fluence value associated with the respective aperture.

In an embodiment, the uncertainty of a radiation dose distribution in the movement direction of the leaves of the leaf pairs of the MLC is determined using:

$$U=\int (\Sigma_i w_i(e_i(x-x_{l,i})+e_i(x_{r,i}-x)))^2 dx,$$

wherein $w_i$ corresponds to the possible fluence value associated with a possible aperture, $e_i(x)$ refers to an uncertainty function defining the distribution of the uncertainty, $x_{l,i}$ and $x_{r,i}$ refer to possible left and right leaf positions of a pair of leaves of the MLC, and x runs over the aperture size in x-direction defined as the movement direction of the leaves of the leaf pair, i.e. the direction in which the position of the leaves can be changed. The above function comprises an integral over x, however, the x-direction can be any direction. The formula above provides the uncertainty for a leaf pair in x-direction, wherein a smaller opening between the leaves of the leaf pair comprise a higher uncertainty.

Moreover, in an embodiment, the above function for the uncertainty can also be expanded to take into account edges with respect to other directions, for instance, edges with respect to a direction perpendicular to the x-direction, i.e. along the y-direction. These uncertainties might comprise other characteristics than the uncertainties in x-direction, for instance, due to other construction constrains of the MLC in this direction. Preferably, the uncertainty of an aperture in y-direction is determined such that apertures with ragged edges have a higher uncertainty compared to apertures with a more rounded opening area.

An uncertainty of a radiation dose distribution taking also the y-direction into account can, for instance, be formulated in accordance with the below explanation. The uncertainty for the lower left edge of the left leaf in a row i can be expressed as $$U=\int_{min\{x_{l,i},x_{l,i-1}\}}^{min\{x_{l,i},x_{r,i-1}\}} [\int_Y e_i(y-y_{l,i,lower}) dy] dx,$$

wherein $y_{l,i}$ is the position of the lower edge of the left leaf of a pair of leaves in row i towards row i−1, $e_i(y)$ refers to an uncertainty function defining the distribution of the uncertainty in y-direction of the lower edge of the leaf, and Y is the domain where the uncertainty function $e_i(y)$ is non-zero. Equivalent formulae can be given for the other edges of the row i, namely:

$$U=\int_{max\{x_{l,i},x_{l,i-1}\}}^{max\{x_{l,i},x_{r,i-1}\}} [\int_Y e_i(y-y_{l,i,lower}) dy] dx,$$

$$U=\int_{min\{x_{l,i},x_{l,i+1}\}}^{min\{x_{l,i},x_{r,i+1}\}} [\int_Y e_i(y-y_{l,i,upper}) dy] dx,$$

$$U=\int_{max\{x_{l,i},x_{l,i+1}\}}^{max\{x_{l,i},x_{r,i+1}\}} [\int_Y e_i(y-y_{l,i,upper}) dy] dx,$$

wherein the uncertainty function $e_i(y)$ can be different for all edges of the leaf pair. The uncertainty in x- and y-direction can then be determined by summing over all occurring terms for all leaf pairs and, for instance, weighting the terms with a respective fluence value.

In an embodiment, the optimization function is indicated by:

$$O=D+\lambda U,$$

wherein D refers to the deviation and $\lambda$ is a weight for weighting the influence of the uncertainty U during the optimization of the optimization function O. The weight $\lambda$ can be determined empirically, for instance, through measurements, and can depend on the radiation therapy protocol that should be used. The weight can be provided to a user, for instance, by providing it on a user interface on a display, and the user can adjust the weight during the planning of the therapy plan, for instance, to achieve a desired compromise between the uncertainty, i.e. quality, of the therapy plan and the meeting of the other objectives of the therapy plan.

In an embodiment, the radiation therapy system is configured to provide the radiation beam from a plurality of directions, wherein the therapy system characteristics providing unit is adapted to provide possible beam directions of the radiation therapy system as characteristics of the radiation therapy system, wherein the radiation dose distribution further depends on a sequence of possible radiation directions, and wherein the uncertainty is determined based on the uncertainty determined for each partial radiation dose distribution defined by a possible direction, a possible aperture and a possible fluence value being part of the sequence defining the radiation dose distribution. For instance, the radiation therapy system can be adapted to provide the radiation therapy from different directions by moving a radiation beam generating unit that is adapted to generate the radiation beam to different positions around the patient. The possible beam direction can then be defined by the possible positions of the radiation beam generating unit and possible angles under which the radiation beam generating unit can provide the radiation beam to the patient. In this embodiment, a radiation therapy plan is defined by a sequence of possible positions, possible apertures and possible fluence values. Based on the possible apertures and possible fluence values associated with a possible direction a partial radiation dose distribution can be determined for each possible direction being part of a sequence of possible directions defining a radiation dose distribution. Moreover, for each of these partial radiation dose distributions an uncertainty can be determined based on the associated possible apertures and the associated fluence values, and the uncertainty of the radiation dose distribution can be determined based on the uncertainties of each partial radiation dose distribution.

In an embodiment, each radiation direction of a possible sequence of radiation directions is associated with at least one possible aperture and at least one possible fluence value defining a radiation dose distribution for the radiation direction, wherein the uncertainty is determined based on a sum of the uncertainties of each partial radiation dose distribution associated with each possible direction of the sequence of possible directions. In particular, in this embodiment the radiation therapy system is adapted to provide the radiation therapy according to a step and shoot protocol as a sequence of a plurality of discrete beam directions, wherein each beam direction is associated with one or more apertures and fluence values. The uncertainty can in such cases be determined based on the sum of uncertainties of each partial radiation dose distribution associated with each possible direction of the sequence of the possible directions defining the radiation dose distribution.

In another embodiment, the radiation therapy system is adapted to continuously change between possible beam directions, leaf positions and fluence values while generating the radiation beam, wherein the uncertainty for a radiation dose distribution resulting from a sequence of continuously changing possible beam directions, leaf positions and fluence values is estimated based on summing over uncertainties determined for partial radiation dose distributions determined for a plurality of directions of the continuously changing sequence of possible directions. The uncertainties determined for a plurality of directions can be propagated into the patient before the summation. Preferably, the radiation therapy system is adapted to provide the radiation therapy according to a volumetric modulated arc therapy protocol such that during the rotation of the radiation beam, i.e. the continuous changing of the beam direction, the leaf positions and fluence values can also be changed continuously. In such a case the radiation dose distribution is obtained by determining partial radiation dose distributions for a set of discrete directions obtained by sampling the continuous movement sufficiently dense, for instance, for every four degrees, and subsequently summing these partial radiation dose distributions. The uncertainty for the radiation dose distribution provided by a continuous sequence according to a volumetric modulated arc therapy protocol can then be determined accordingly, i.e. can be estimated based on summing over uncertainties determined for some partial radiation dose distributions provided from a plurality of beam directions and by summing the uncertainties over all beam directions.

In an embodiment, the uncertainty is further determined taking into account uncertainties resulting from a small arc approximation used for determining the radiation dose distribution from the sequence of continuously changing possible beam directions, leaf positions and fluence values. A detailed explanation of the small arc approximation for determining a radiation dose distribution in cases in which radiation therapy is provided according to a volumetric modulated arc therapy protocol can be found, for instance, in the articles "Some considerations concerning volume-modulated arc therapy: a stepping stone towards a general theory" by S. Webb et al., Physics in Medicine & Biology, volume 54, pages 4345-4360 (2009), "Initial dosimetric evaluation of SmartArc—a novel VMAT treatment planning module implemented in a multi-vendor delivery chain" by V. Feygelman et al, Journal of Applied Clinical Medical Physics, volume 11, pages 99-116 (2010), and "The effect of MLC speed and acceleration on the plan delivery accuracy of VMAT" by J. Park et al, The British Journal of Radiology, volume 88, 1049 (2015).

Small arc approximations can introduce a further uncertainty into the radiation dose distribution for cases in which the leaves have to move rapidly during the providing of the radiation therapy. Determining the uncertainty for the radiation dose distribution further based on the uncertainties resulting from small arc approximation can lead to a further optimization of the radiation therapy plan for cases of volumetric modulated arc therapy. For instance, the uncertainty caused by the small arc approximation can be calculated based on calculating a difference between a radiation dose distribution calculated with the small arc approximation using a first angular spacing, for instance, an angular spacing of four degrees, with the radiation dose distribution estimated with a small arc approximation using a second angular spacing, for instance, two degrees angular spacing. The uncertainty in this case describes the uncertainty of approximating a continuous integral by a summation from discrete angular positions as is done by the small arc approximation. One possibility to determine the uncertainty from this effect is to construct a set of uncertainty functions with adaptable width for each interval between consecutive discrete sampling points, i.e. between different angular positions, wherein the width corresponds to the amount of continuous movement of the corresponding leaf between the two different angular positions. The determined uncertainty functions can then be associated with the center of the interval spanning from one sampling point to the next. This allows to determine the uncertainty of the small arc approximation in accordance with the above described determination of the uncertainty of an MLC aperture. A weighting in this case can be based, for example, on a linear combination of the fluence values of the neighboring MLC apertures.

In another aspect of the invention, a radiation therapy system for providing a radiation therapy to a patient is presented, wherein the radiation therapy system comprises a) a radiation beam generating unit adapted for generating a radiation beam with at least one possible fluence value, wherein the radiation beam generating unit is further adapted to provide the radiation beam to a patient, b) an MLC comprising a plurality of moveable leaves being movable to a plurality of possible leaf positions for shaping an aperture of the MLC such that the beam of radiation is shaped by the aperture before being provided to the patient, c) a radiation therapy plan determination system according to claim 1 for determining an optimized radiation therapy plan comprising a sequence of optimized possible leaf positions and optimized possible fluence values, and d) a radiation therapy controlling unit for controlling the radiation beam generating unit and the MLC such that the therapy plan is provided to the patient.

In another aspect of the invention, a radiation therapy plan determination method is presented, wherein the radiation therapy determination method is adapted to determine a radiation therapy plan for a radiation therapy system comprising a MLC, wherein the MLC comprises a plurality of moveable leaves for shaping an aperture of the MLC such that a radiation beam is shaped by the aperture before being provided to a patient, wherein the radiation therapy plan determination method comprises a) providing characteristics of the therapy system, wherein the characteristics comprise possible leaf positions defining possible apertures of the MLC and possible radiation fluence values that are providable by the radiation therapy system, b) providing planning objectives, wherein the planning objectives are indicative of a desired therapeutic radiation dose distribution that should be provided to the patient, c) providing an optimization function being indicative of a deviation of a radiation dose distribution from the planning objectives, wherein the radiation dose distribution depends on a sequence of possible apertures defined by the leaf positions and possible radiation fluence values, and wherein the optimization function is further indicative of an uncertainty of the radiation dose distribution at edges of the possible apertures, and d) determining an optimized therapy plan by determining a sequence of possible apertures and possible radiation fluence values for which the optimization function is optimized, wherein the sequence of optimized possible apertures and optimized possible fluence values defines the optimized therapy plan.

In another aspect of the invention, a computer program for determining a radiation therapy plan for a radiation therapy system comprising an MLC is presented, wherein the computer program comprises program code means for causing the radiation therapy plan determination system described above to carry out the steps of the radiation therapy plan determination method as described above when the computer program is executed by the system.

It shall be understood that the radiation therapy plan determination system of claim 1, the radiation therapy system of claim 13, the radiation therapy plan determination method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
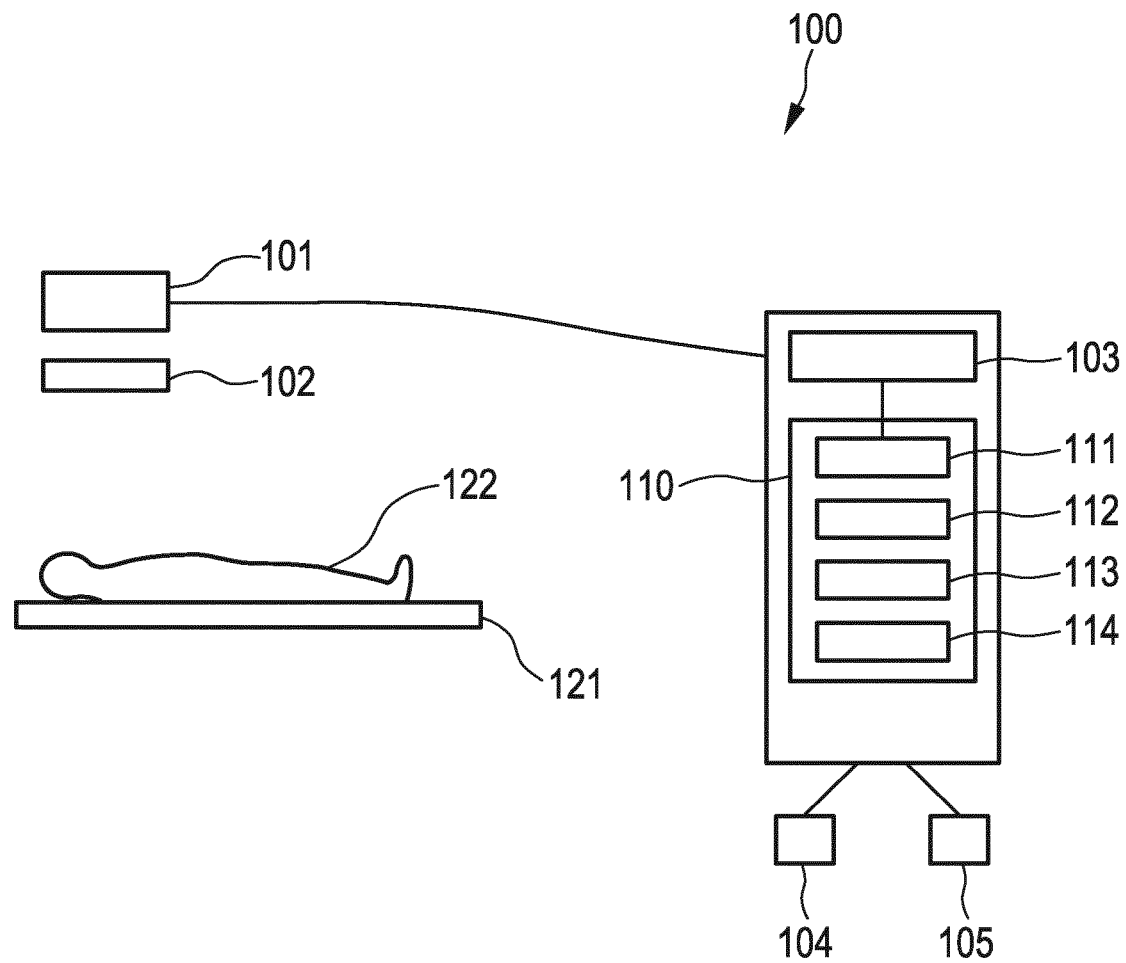
FIG. 1 shows schematically and exemplarily an embodiment of a radiation therapy system for providing a radiation therapy to a patient comprising a radiation therapy plan determination system according to the invention.

FIG. 1 shows schematically and exemplarily an embodiment of a radiation therapy system comprising a radiation therapy plan determination system according to the invention. In the following embodiments the radiation therapy system 100 comprises a radiation beam generating unit 101 adapted to generate a radiation beam that is provided to a patient 122 lying on a patient table 121. The radiation beam generating unit 101 is adapted to generate the radiation beam with at least one possible fluence value. Preferably, the radiation beam generating unit 101 is adapted to generate the radiation beam with a plurality of different fluence values.

Figure 3:
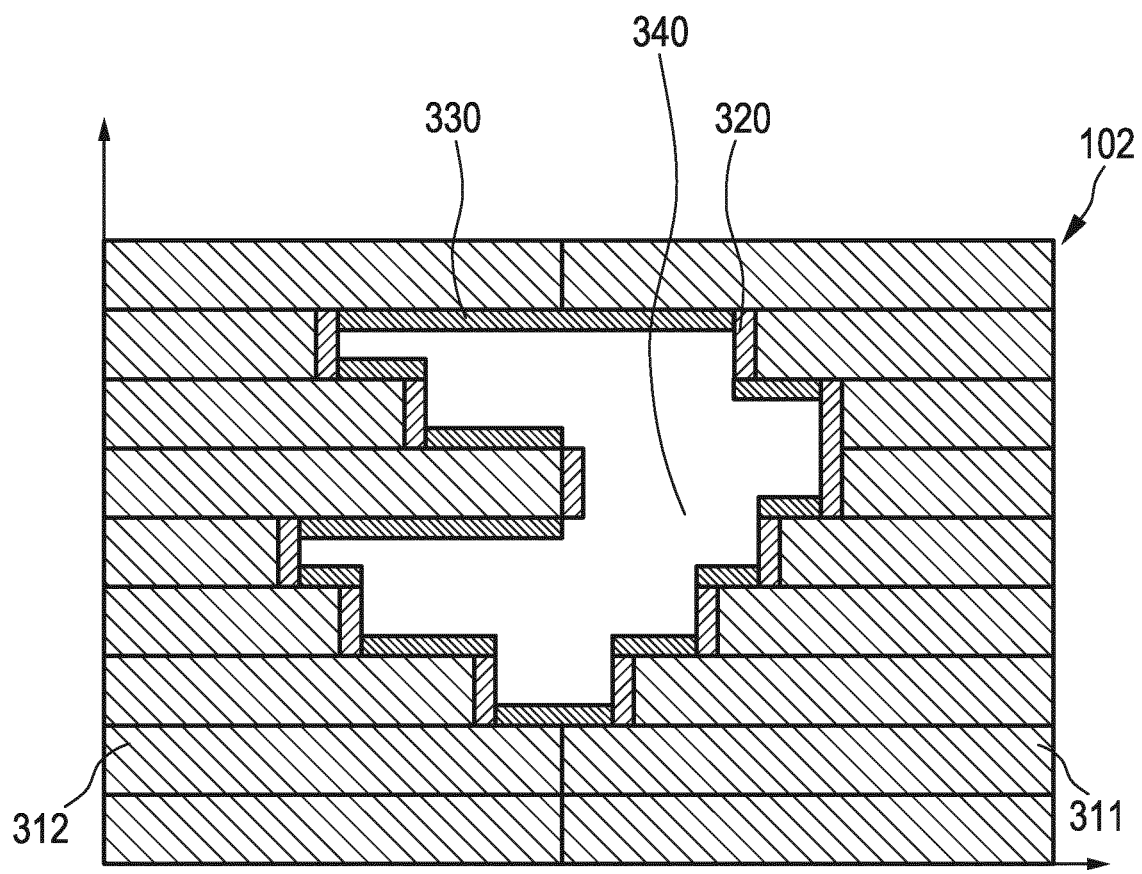
FIG. 3 shows schematically and exemplarily a principle for determining the uncertainties for edges of an MLC aperture.

Further, the radiation therapy system 100 comprises an MLC 102 comprising a plurality of movable leaves being moveable to a plurality of possible leaf positions for shaping an aperture of the MLC 102. A schematic example of an MLC 102 is given, for instance, in FIG. 3 showing a plurality of leaves, for instance, leaf pair 311, 312, and the aperture 340 formed by the leaves. The MLC 102 is provided by the radiation therapy system 100 such that it is provided between the radiation beam generating unit 101 and the patient 122 lying on the patient table 121. The MLC 102 is adapted to shape the radiation beam provided by the radiation beam generating unit 101 in accordance with the aperture formed by the MLC 102 before the radiation beam is provided to the patient 122. Based on the radiation generated by the radiation beam generating unit 101 the MLC 102 is adapted such that the radiation cannot pass regions in which leaves of the MLC 102 are provided within the radiation beam. Thus, the radiation beam can only pass through the aperture of the MLC 102.

In this embodiment the radiation therapy system 100 further comprises a radiation therapy controlling unit 103 which is adapted to control the radiation beam generating unit 101 and the MLC 102 in accordance with a radiation therapy plan. In particular, the radiation therapy plan comprises a sequence of possible leaf positions of the MLC 102 and of possible radiation fluence values that can be generated by the radiation beam generating unit 101. The radiation therapy controlling unit 103 is then adapted to provide the radiation therapy plan to the patient 122 by controlling the radiation beam generating unit 101 to generate the radiation beam in accordance with the sequence of fluence values and by controlling the MLC 102 in accordance with the sequence of apertures or leaf positions in accordance with the radiation therapy plan.

In this embodiment the radiation therapy system 100 comprises a radiation therapy plan determination system 110. The radiation therapy plan determination system 110 is adapted to provide an optimized radiation therapy plan to the radiation therapy controlling unit 103, wherein the radiation therapy controlling unit 103 is then adapted to control the radiation beam generating unit 101 and the MLC 102 in accordance with the optimized radiation therapy plan.

The radiation therapy plan determination system 110 comprises a therapy system characteristics providing unit 111, a planning objectives providing unit 112, an optimization function providing unit 113 and a therapy plan optimization unit 114.

The therapy system characteristics providing unit 111 is adapted to provide the characteristics of the radiation therapy system 100. In particular, the therapy system characteristics providing unit 111 is adapted to provide as characteristics of the radiation therapy system 100 the possible leaves positions defining the possible apertures of the MLC 102 and the possible radiation fluence values of the radiation generating unit 101. The therapy system characteristics providing unit 111 can provide the possible leaf positions, for instance, as possible coordinates of the tips of the leaves of the MLC 102. Moreover, the therapy system characteristics providing unit 111 can provide the possible radiation fluence values as a list of the possible radiation fluence values or of a range of the possible radiation fluence values that can be generated by the radiation beam generating unit 101.

The therapy system characteristics providing unit 111 can also be adapted to provide additional characteristics of the radiation therapy system 100. For instance, if the radiation system 100 is adapted to further provide the radiation from different directions, the therapy system characteristics providing unit 111 can be adapted to provide as characteristic the possible beam directions of the radiation therapy system 100.

In this embodiment, the therapy system characteristics providing unit 111 is adapted to receive the therapy system characteristics from a storage unit on which the radiation therapy system characteristics are stored, for instance, in form of a manual or in form of a list of characteristics. However, in other embodiments the therapy system characteristics can also be provided by a user into an input unit and can then be received by the therapy system characteristics providing unit 111 from the input unit.

The planning objectives providing unit 112 is adapted to provide planning objectives for the radiation therapy that should be provided to the patient 122. For instance, the planning objectives providing unit 112 can be adapted to communicate with a display unit 104 and/or an input unit 105, like a keyboard or a mouse, for receiving the planning objective from a user, like a radiologist. The planning objectives are indicative of a desired therapeutic radiation dose distribution that should be provided to the patient 122. A radiologist can, for instance, determine on a computer tomography image of the patient 122 a tumor region that should be irradiated with a predetermined radiation dose during the radiation therapy. Moreover, the radiologist can determine a region of healthy tissue around the tumor that should receive as little radiation as possible and can further provide a radiation dose threshold for this region that should not be exceeded. Additionally, the radiologist can provide a region comprising an organ like a main artery or a part of the brain that should not receive any radiation at all. The planning objectives provided by the radiologist are indicative of a desired therapeutic radiation dose distribution that should be provided to the patient 122. However, due to the specific construction of the radiation therapy system 100 it might not be possible to provide exactly this desired radiation dose distribution to the patient 122 such that a therapy plan has to be determined that provides a radiation dose distribution to the patient 122 that fulfils the planning objectives as good as possible. In some cases, the radiologist might further provide weights to the planning objectives that are indicative of an importance of the respective planning objectives and with which the optimization process during the determination of the optimized therapy plan can be influenced.

The optimization function providing unit 113 is adapted to provide an optimization function that is indicative of a deviation of a radiation dose distribution from the planning objectives. Moreover, the optimization function is further indicative of an uncertainty of the radiation dose distribution at edges of the possible apertures, for instance, due to scatter radiation or uncertainties in the position of the leaves of the MLC 102. These uncertainties of the radiation dose distribution at edges of the possible apertures can be calculated based on the possible leaf positions of the MLC 102 and the possible radiation fluence values that define a radiation dose distribution. An example of the general principles underlying the idea of taking uncertainties at edges of the apertures of the MLC 102 into account will be explained in the following with respect to FIGS. 2 and 3.

Figure 2:
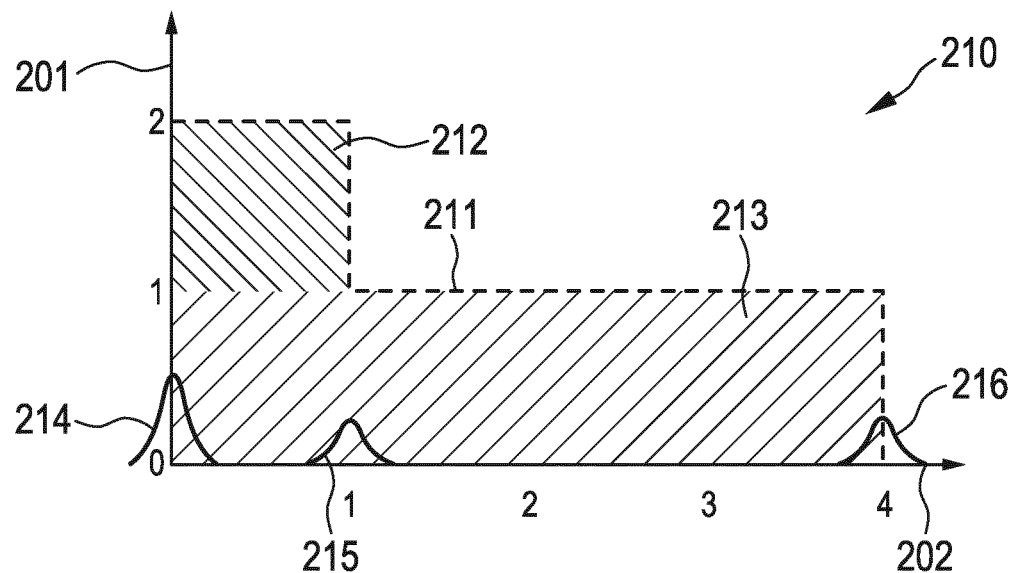
FIG. 2 shows schematically and exemplarily principles underlying the determination of an uncertainty for a radiation dose distribution.
Figure 2:
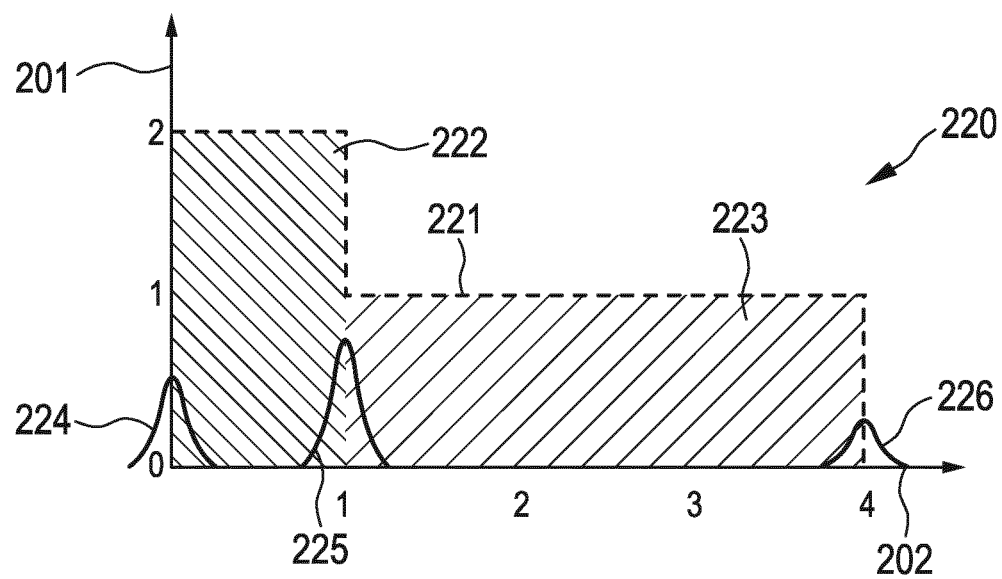

FIG. 2 shows two schematic examples 210 and 220, wherein in these examples 210, 220 the radiation dose distribution 211, 221 is provided using different sequences of apertures. The graphs shown for the two examples 210 and 220 comprise a y-axis 201 indicative of a fluence value 211 received by the patient 122 and an x-axis 202 indicative of the x-position of the two leaves forming the respective aperture for which the radiation dose distribution is shown. The radiation dose distributions 211, 221 of both examples 220, 222 are similar and are formed by a sequence of two apertures, for instance, apertures 212 and 213, wherein each aperture is associated with one fluence value.

In the first example 210 the radiation dose distribution 211 is achieved by a first aperture 213 comprising leaf positions of zero for the left leaf and of four for the right leaf and by a second aperture 212 with leaf positions zero for the left leaf and one for the right leaf. Both apertures 213 and 212 are associated with the same fluence value. For this case the uncertainty of the radiation dose distribution at the edges of the apertures are exemplarily indicated by the curves 214, 215 and 216 along the x-axis. At each position of the radiation dose distribution 211 at which during the sequence of apertures 212, 213 an edge of a leaf an x-direction can be found an uncertainty is provided in accordance with uncertainty functions 215 and 216. At position zero, uncertainty function 214 is twice as high as uncertainty functions 215 and 216, since at this point both apertures 212, 213 of the sequence of apertures comprise an edge in x-direction such that the uncertainty functions at this position are combined, in particular, summed up.

In the second example 220 the radiation dose distribution 221 is achieved by providing a sequence of apertures 222 and 223. Aperture 223 is defined by a position of one of the left leaf and a position of four of the right leaf for this aperture 223. Aperture 222 is defined by a position of zero of the left and a position of one of the right leaf and is associated with a fluence value twice as high as for aperture 223. As can be seen by the uncertainties 224, 225 and 226 exemplarily indicated at the x-axis 202, the uncertainties for this radiation dose distribution are completely different from the uncertainties for the first radiation dose distribution 211. In particular, the uncertainty 224 is twice as high as the uncertainty 226, although only one edge, i.e. the edge of aperture 222, is positioned at position zero during the sequence. However, since the fluence value for the aperture 222 is twice as high as the fluence value for the aperture 223, also the uncertainties associated with apertures 222 are twice as high as the uncertainties associated with aperture 223. This also leads to uncertainty 225, for which further the presence of two edges at position one during the sequence has to be taken into account, leading to an uncertainty 225 three times as high as uncertainty 226.

It is clear from this schematic example that, although both apertures and fluence value sequences lead to the same radiation dose distributions 211, 221, the uncertainty of the radiation dose distribution in the second example 220, i.e. for the second sequence, is much higher than for the first example 210, i.e. for the first sequence. Based on this principle it is clear that the uncertainties of the radiation dose distribution received by a patient 122 during the provision of a radiation therapy plan could be decreased if a radiation therapy plan in accordance with the first example 210 is chosen as optimized radiation therapy plan.

As an example, this principle can mathematically be formulated as described in the following. Considering for this mathematical example only the edges of the apertures in x-direction, a possible MLC aperture i can be described by $$b_i(x) = H(x - x_{l,i}) \cdot H(x_{r,i} - x),$$

wherein H(x) refers to the Heavyside step function and $x_{l,i}$ and $x_{r,i}$ refer to the possible left and right leaves positions of a pair of leaves of an MLC 102 for a possible aperture $b_i(x)$. In this example, the planning objectives can be considered in the form of a desired radiation dose distribution f(x). In this case a function D being indicative of the deviation of a radiation dose distribution from the planning objectives can be formulated as $$D = \int (f(x) - \Sigma_i w_i \cdot b_i(x))^2 dx \quad w_i \geq 0,$$

wherein $w_i$ refers to the possible fluence value associated with the possible aperture $b_i(x)$. The sum over i indicates the sum over all partial radiation dose distributions defined by possible apertures and fluence values that are part of the sequence defining the radiation dose distribution.

In this example, the uncertainty U can be defined by using an uncertainty function for each edge $e_i(x)$. The uncertainty can then be indicated, i.e. modeled, by $$U=\int (\Sigma_i w_i(e_i(x-x_{l,i})+e_i(x_{r,i}-x)))^2 dx.$$

In a preferred example, the uncertainty function can be chosen as a Gaussian function. The optimization function can then be provided as $O=D+\lambda U$, wherein $\lambda$ denotes a weight for weighting the influence of the uncertainty U during the optimization of the optimization function O. In this mathematical formulation the optimization function can be minimized for providing the optimized therapy plan.

During the minimizing of this optimization function the uncertainty at the edges of the apertures is taken into account and leads to a preference of radiation therapy plans, i.e. possible aperture and possible fluence value sequences, comprising as little uncertainty as possible. In particular, coming back to the example given in FIG. 2, optimizing such an optimization function as provided above would lead in this example to a radiation therapy plan in accordance with the first example 210 and not in accordance with the second example 220.

FIG. 3 shows exemplarily an MLC 102 comprising leaf pairs arranged along an axis of the MLC 102, like leaf pair formed by leafs 312 and 311, forming an aperture 340. The uncertainty calculated in accordance with the above formula refers in this example to the edge regions in x-direction denoted with the numeral 320. However, the formula given above can also be expanded to take into account edge regions 330 between two apertures in y-direction. The uncertainties for this case can be formulated in accordance with the uncertainties formulated for the edges in x-direction.

A therapy plan optimization unit 114 is then adapted to optimize the optimization function, i.e. to determine a sequence of possible apertures and possible radiation fluence values, for which the optimization function is optimized. The therapy plan optimization unit 114 can optimize the optimization function in accordance with known optimization algorithms, like, for instance, iterative optimization algorithms. Since the uncertainty of the radiation dose distribution at edges of possible apertures is taken into account, the optimized therapy plan determined by the therapy plan optimization unit 114 will comprise as little uncertainty as possible for the radiation dose distribution that is received by the patient 122.

Figure 4:
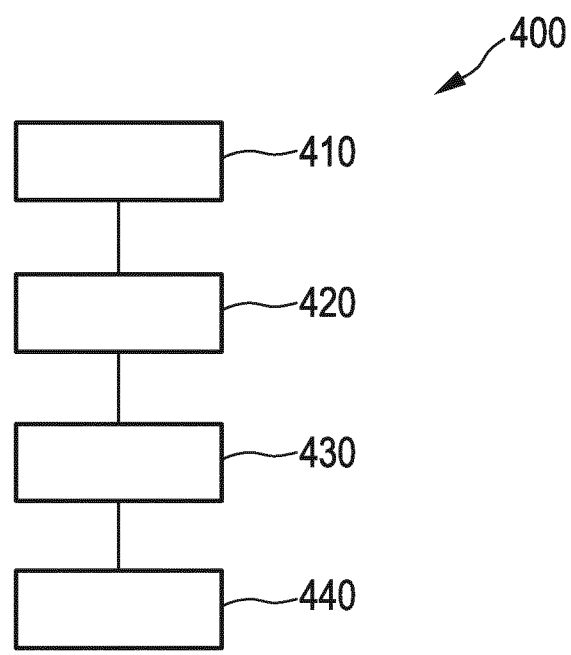
FIG. 4 shows a flowchart exemplarily illustrating an embodiment of a method for determining a radiation therapy plan.

FIG. 4 shows a flowchart exemplarily illustrating an embodiment of a method for determining a radiation therapy plan. The radiation therapy plan determination method 400 comprises a first step 410 of providing characteristics of the radiation therapy system 100. The characteristics comprise possible leaf positions defining possible apertures of the MLC 102 and possible radiation fluence values that are providable by the radiation therapy system 100, for instance, by the radiation beam generating unit 101. In a second step 420 planning objectives are provided, wherein the planning objectives are indicative of a desired therapeutic radiation dose distribution that should be provided to the patient 122. An optimization function is provided in step 430. The optimization function can be provided in accordance with the principles laid out above and is indicative of a deviation of a radiation dose distribution from the planning objectives and of an uncertainty of the radiation dose distribution at edges of the possible apertures. In the last step 440 an optimized therapy plan is determined by determining a sequence of possible apertures and possible radiation fluence values for which the optimization function is optimized. The sequence of optimized possible apertures and optimized possible fluence values then defines the optimized therapy plan that can be provided to the patient 122 using radiation therapy system 100.

Although in the above described embodiments the radiation beam was only provided from one direction to the patient 122, in other embodiments the radiation therapy system 100 can be adapted to further provide the radiation beam from different directions to the patient 122. For instance, the radiation therapy system 100 can be adapted to provide the radiation therapy in accordance with a step and shoot protocol, wherein a sequence of radiation beam directions with associated possible apertures and associated possible radiation fluence values is provided as radiation therapy plan to the patient 122. In this case the optimization function can be determined, for instance, in accordance with the above exemplary functions as $O=D+\lambda \Sigma_j U_j$, wherein j refers to the different beam directions of the sequence, i.e. the radiation therapy plan in accordance to the step and shoot protocol. Accordingly, the uncertainty of a radiation dose distribution defined by a sequence of possible beam directions, apertures and fluence values can be determined as a sum over the uncertainties of partial radiation dose distributions defined by the apertures and fluence values associated with the possible beam directions of the sequence.

Moreover, the radiation therapy system 100 can be adapted to provide the radiation therapy in form of a volumetric modulated arc therapy, wherein in this form of therapy the radiation therapy plan is provided as a continuous sequence of beam directions and associated possible apertures and possible radiation values, i.e. during the movement of the radiation beam generation unit 101 and the MLC 102 around the patient 122 the radiation is continuously emitted towards the patient 122 and thus also during changes from one aperture of the sequence and one fluence value of the sequence to another aperture or another fluence value of the sequence. In this case one possibility to calculate the uncertainty is to propagate the uncertainty from the fluence plane, i.e. the two-dimensional space representing the MLC as shown in FIG. 3, into the patient body and to accumulate the uncertainty for the different beam directions of a sequence by integrating the uncertainty over the patient body. The resulting uncertainty can then be added to the deviation D to provide the optimization function O in the same way as described above.

In this embodiment, additionally uncertainties caused by the approximations used for determining the radiation dose distribution for a volumetric modulated arc therapy protocol can be taken into account when determining the uncertainty. These uncertainties can, for instance, be caused by the movement of the leaves, in particular, since the exact movement and velocity of rapidly moving leaves comprises some uncertainty due to the constructional limitations of the MLC. These uncertainties can be determined, for instance, in case of a small arc approximation by calculating a first radiation dose distribution using a first angular spacing in the small arc approximation and then calculating a second radiation dose distribution by assuming a second angular spacing in the small arc approximation and determining the difference between the first and the second radiation dose distribution. This difference is indicative for the uncertainty that is introduced by using the small arc approximation for calculating the radiation dose distribution. For instance, the total radiation dose distribution can be represented by two slightly different approximations:

$$D \approx \Sigma_i w_{2i} d_{2i} \approx \Sigma_j w'_j d_j,$$

wherein $d_{2i}$ with $i=0, \ldots n$ refers to the partial radiation dose distributions determined for a first angular spacing, $d_j$ with $j=0, \ldots 2n$ refers to the partial radiation dose distributions of the same radiation therapy plan determined using a second angular spacing being finer than the first angular spacing, and $w_{2i}$ and $w_j$ referring to the corresponding fluence values. The difference between these approximations for the total radiation dose distribution can be used as a measure for uncertainty due to the finite approximations. Taking the square of the difference and multiplying it with some appropriate scale factor can be used as three-dimensional uncertainty function in the patient domain which can be used for determining the uncertainty, as described above, by integrating over the patient domain.

The influence of an MLC in general and the leaf positions of the MLC in particular on a simulated radiation dose distribution for radiation therapy plan optimization can often only be described approximately. In particular, the leaf tips can cause an uncertainty, for instance, due to scattered radiation and positioning inaccuracy. This effect is amplified if two MLC apertures are abutting, for instance, in a sequence of apertures defining a radiation therapy plan. This uncertainty effect can be decreased if a sequence comprising one large MLC aperture shape is preferred over a sequence comprising two smaller MLC aperture shapes that should theoretically result in the same radiation dose distribution.

Current radiation therapy plan optimization algorithms do not account for the above explained uncertainty of a radiation dose distribution, but use empirical rules that prefer, for instance, plans with less monitor units, to generate good quality plans. This makes it difficult to design algorithms that generate radiation therapy plans defining a sequence of MLC aperture shapes that satisfy the multitude of empirical expectations of clinicians and dosimetrists regarding the accuracy of a good radiation therapy plan.

A basic idea of the invention is to use, apart from the simulated radiation dose distribution, i.e. the radiation dose distribution that should be optimized subject to planning objectives, the uncertainty of the radiation dose distribution as an additional criterion during radiation therapy plan optimization. The uncertainty may be modelled for each leaf tip of an MLC by a Gaussian type function weighted with a fluence value associated with a corresponding MLC aperture, centered at the leaf tip, and with a width corresponding to the anticipated uncertainty. For using the uncertainty, the objective function to be minimized is penalized by adding a metric of the uncertainty. For instance, when approximating a continuous radiation dose distribution resulting from a fluence map optimization with discrete MLC apertures during leaf sequencing, the result is penalized with the weighted mean-squared dose uncertainty, i.e. sequences comprising MLC apertures resulting in less uncertainty or a more homogeneous distribution of uncertainty are preferred. Similarly, in direct machine parameter optimization leading to an optimized therapy plan for a step and shoot protocol, a weighted metric of the uncertainty in the fluence plane can be added to the objective function, i.e. optimization function, to be minimized. For volumetric modulated arc therapy, dose uncertainty can be projected into a volume representing the body of a patient and accumulated, for instance, similarly to the dose itself, wherein the objective function, i.e. optimization function, is penalized by a weighted metric of the uncertainty accumulated over the body volume and/or target and risk organs.

For a step and shoot protocol, for instance, a tumor is irradiated using different radiation beam directions, wherein each of the beam directions can be associated with a plurality of MLC apertures with associated fluence values. In one embodiment, using direct machine parameter optimization (DMPO) for optimizing the optimization function, the radiation dose distribution in the patient body can be determined given the machine parameters, i.e. the possible leaf positions for the possible MLC apertures and the possible fluence values associated with the MLC apertures, and planning objectives, for instance, a minimal radiation dose in the tumor or a maximal radiation dose in a risk organ, wherein the objective function, i.e. optimization function, is minimized in dependence of the machine parameters. The objective function can quantify the deviation of the planning objectives for a desired radiation dose distribution from a simulated radiation dose distribution. The uncertainty can be taken into account by minimizing the optimization function being defined also by a sum of the uncertainty over all beam directions and comprising a weight for weighting the uncertainty.

In volumetric modulated arc therapy (VMAT), a linear accelerator, i.e. radiation beam generating unit, is rotated around the patient while the leaves in the collimator are moving and radiation is continuously emitted towards the target, for instance, tumor. In this case the radiation dose distribution uncertainty can be computed in a different way as for a step and shoot protocol where radiation is emitted through multiple MLC apertures from the same direction. In this case, the uncertainty can be propagated from a fluence plane into the patient body and accumulated for the different beam directions similarly as the dose in the patient body can be computed in this case. A measure of the uncertainty can then be computed by integrating uncertainty over the irradiated part of the patient body, the target region and/or regions corresponding to the risk organs. Again, the resulting uncertainty can then be added to the objective function to account for the uncertainty in the radiation therapy plan generation by minimization.

In the case of VMAT, additional uncertainties in the radiation dose distribution may be taken into account that result, for instance, from the small arc approximation. This approximation can lead, for instance, to inaccuracies during the estimation of radiation dose distributions in the case of rapidly moving leaves. The difference between a dose computation with four degrees versus two degrees angular spacing may, for instance, be used to quantify the uncertainty over the irradiated part of the patient body, the target region and/or regions corresponding to the risk organs and used as a measure of the uncertainty. Generally, information about the uncertainty may be displayed by a user interface, i.e. a display, to support dosimetrists, physicists and clinicians with plan generation and quality assurance.

Although in the above embodiments the radiation therapy plan determination system was part of the radiation therapy system, in other embodiments the radiation therapy plan determination system can be a stand-alone system, or a system that is connected to a plurality of different radiation therapy systems.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of radiation therapy system characteristics, planning objectives, and objective functions or procedures like the determination of the optimized therapy plan performed by one or several units or devices can be performed by any other number of units or devices. For instance, these procedures can be carried out by a single device. These procedures can be implemented as program code means of a computer program and/or as a dedicated hardware.

A computer program may be stored/distributed on a suitable medium such as an optical storage medium or a solid state medium, supplied together with or as part of other hardware but may also be distributed on other forms such as via the internet or other wireless communication systems.

Any reference signs in the claims should not be construed as limiting the scope.

The invention relates to a system for determining a radiation therapy plan for a radiation therapy system, comprising a multi-leaf collimator. The radiation therapy plan determination system comprises a therapy system characteristics providing unit, wherein the characteristics comprise possible leaf positions and possible radiation fluence values, a planning objectives providing unit, wherein the planning objectives are indicative of a desired therapeutic radiation dose distribution, an optimization function providing unit, wherein the optimization function is indicative of a deviation of a radiation dose distribution from the planning objectives and of an uncertainty of the radiation dose distribution at edges of the possible apertures, and a therapy plan optimization unit adapted to determine a sequence of possible apertures and possible radiation fluence values for which the optimization function is optimized. Thus, an optimal therapy plan can be provided for each individual patient.

The invention claimed is:

1. A Radiation therapy plan determination system for determining a radiation therapy plan for a radiation therapy system comprising a multi-leaf collimator (MLC), wherein the MLC comprises a plurality of moveable leaves for shaping an aperture of the MLC such that a radiation beam is shaped by the aperture before being provided to a patient, and wherein the radiation therapy plan determination system comprises:
  a therapy system characteristics providing unit for providing multiple characteristics of the radiation therapy system, wherein the multiple characteristics comprise possible leaf positions defining possible apertures of the MLC and possible radiation fluence values that are providable by the radiation therapy system;
  a planning objectives providing unit providing one or more planning objectives, wherein the one or more planning objectives are indicative of a desired therapeutic radiation dose distribution that should be provided to the patient;
  an optimization function providing unit for providing an optimization function, wherein the optimization function is indicative of a deviation of a radiation dose distribution from the one or more planning objectives, wherein the radiation dose distribution depends on a sequence of possible apertures defined by the possible leaf positions and possible radiation fluence values, and wherein the optimization function is further indicative of an uncertainty of the radiation dose distribution at edges of the possible apertures; and
  a therapy plan optimization unit for determining an optimized therapy plan, wherein the therapy plan optimization unit is adapted to determine the sequence of possible apertures and the possible radiation fluence values for which the optimization function is optimized, and wherein the sequence of optimized possible apertures and the optimized possible radiation fluence values defines the optimized therapy plan.

2. The radiation therapy plan determination system according to claim 1, wherein the uncertainty of the radiation dose distribution is determined based on the possible leaf positions of the MLC defining the possible apertures and based on the possible radiation fluence values on which the radiation dose distribution depends.

3. The radiation therapy plan determination system according to claim 2, wherein the therapy plan optimization unit is adapted to determine the sequence of possible apertures and the possible radiation fluence values for which the optimization function is optimized such that the sequence of optimized possible apertures and the optimized possible radiation fluence values is the optimized therapy plan that leads to a radiation dose distribution with less uncertainty.

4. The radiation therapy plan determination system according to claim 1, wherein the uncertainty for a radiation dose distribution is modeled based on an uncertainty function centered at, at least one edge of each possible aperture, and wherein the uncertainty function of a respective edge comprises a width corresponding to an anticipated uncertainty for the respective edge.

5. The radiation therapy plan determination system according to claim 4, wherein the uncertainty function of each edge of the at least one edge of each possible aperture is weighted with a possible fluence value that is associated with the possible aperture to which the respective edge belongs.

6. The radiation therapy plan determination system according to claim 1, wherein the uncertainty of a radiation dose distribution in a movement direction of the leaves of one or more leaf pairs of the MLC is determined using:

$$U = \int (\Sigma_i w_i \, (e_i(x-x_l,i) + e_i(x_r,i-X)))^2 \, dx,$$

wherein $w_i$ corresponds to the possible radiation fluence value associated with a possible aperture, $e_i(x)$ refers to an uncertainty function defining the distribution of the uncertainty, and $x_1,i$ and $x_r,i$ refer to possible left and right leaf positions of a particular pair of leaves of the MLC and x runs over an aperture size in x-direction defined as the movement direction of the leaves of the particular pair of leaves.

7. The radiation therapy plan determination system according to claim 1, wherein the uncertainty function is a Gaussian type function.

8. The radiation therapy plan determination system according to claim 7, wherein the optimization function is defined as:

$$O = D + \lambda U,$$

wherein D refers to the deviation and $\lambda$, is a weight for weighting an influence of the uncertainty U during the optimization of the optimization function, O.

9. The radiation therapy plan determination system according to claim 1, wherein the radiation therapy system is configured to provide the radiation beam from a plurality of directions, wherein the therapy system characteristics providing unit is adapted to provide possible beam directions of the radiation therapy system a particular characteristic of the one or more characteristics of the radiation therapy system, wherein the radiation dose distribution further depends on a sequence of possible radiation directions, and wherein the uncertainty is determined based on the uncertainty determined for each partial radiation dose distribution defined by a possible direction, a possible aperture and a possible radiation fluence value being part of the sequence defining the radiation dose distribution.

10. The radiation therapy plan determination system according to claim 9, wherein each radiation direction of a possible sequence of radiation directions is associated with at least one possible aperture and at least one possible radiation fluence value defining a radiation dose distribution for the radiation direction, and wherein the uncertainty is determined based on a sum of the uncertainties of each partial radiation dose distribution associated with each possible direction of the sequence of possible directions.

11. The radiation therapy plan determination system according to claim 1, wherein the radiation therapy system is adapted to continuously change between possible beam directions, leaf positions and radiation fluence values while generating the radiation beam, wherein the uncertainty for a radiation dose distribution resulting from a sequence of continuously changing possible beam directions, leaf positions and radiation fluence values is estimated based on summing over uncertainties determined for partial radiation dose distributions determined for a plurality of directions of the sequence of continuously changing possible beam directions.

12. The radiation therapy plan determination system according to claim 11, wherein the uncertainty is further determined taking into account uncertainties resulting front a small arc approximation used for determining the radiation dose distribution from the sequence of continuously changing possible beans directions, leaf positions and fluence values.

13. A radiation therapy system for providing a radiation therapy to a patient, the radiation therapy system comprising:
   a radiation beam generating unit adapted for generating a radiation beam with at least one possible radiation fluence value, wherein the radiation beam generating unit is further adapted to provide the radiation beam to a patient;
   a multi-leaf collimator (MLC) comprising a plurality of moveable leaves being movable to a plurality of possible leaf positions for shaping an aperture of the MLC such that the radiation beam is shaped by the aperture before being provided to the patient;
   a radiation therapy plan determination system for determining an optimized radiation therapy plan comprising a sequence of optimized possible leaf positions and optimized possible radiation fluence values; and
   a radiation therapy controlling unit for controlling the radiation beam generating unit and the MLC such that the therapy plan is provided to the patient.

14. The radiation therapy system of claim 13, wherein the radiation therapy plan determination system comprises:
   a therapy system characteristics providing unit for providing multiple characteristics of the radiation therapy system, wherein the multiple characteristics comprise possible leaf positions defining possible apertures of the MLC and possible radiation fluence values that are providable by the radiation therapy system;
   a planning objectives providing unit providing one or more planning objectives, wherein the one or more planning objectives are indicative of a desired therapeutic radiation dose distribution that should be provided to the patient;
   an optimization function providing unit for providing an optimization function, wherein the optimization function is indicative of a deviation of a radiation dose distribution from the one or more planning objectives, wherein the radiation dose distribution depends on a sequence of possible apertures defined by the possible leaf positions and possible radiation fluence values, and wherein the optimization function is further indicative of an uncertainty of the radiation dose distribution at edges of the possible apertures; and
   a therapy plan optimization unit for determining an optimized therapy plan, wherein the therapy plan optimization unit is adapted to determine the sequence of possible apertures and the possible radiation fluence values for which the optimization function is optimized, and wherein the sequence of optimized possible apertures and the optimized possible radiation fluence values defines the optimized therapy plan.

15. The radiation therapy system of claim 14, wherein the uncertainty of the radiation dose distribution is determined based on the possible leaf positions of the MLC defining the possible apertures and based on the possible radiation fluence values on which the radiation dose distribution depends.

16. The radiation therapy system of claim 14, wherein the therapy plan optimization unit is adapted to determine the sequence of possible apertures and the possible radiation fluence values for which the optimization function is optimized such that the sequence of optimized possible apertures and the optimized possible radiation fluence values is the optimized therapy plan that leads to a radiation dose distribution with less uncertainty.

17. A Radiation therapy plan determination method for determining a radiation therapy plan for a radiation therapy system comprising a multi-leaf collimator (MLC) wherein the MLC comprises a plurality of moveable leaves for shaping an aperture of the MLC such that a radiation beam is shaped by the aperture before being provided to a patient, the radiation therapy plan determination method comprising:
   providing multiple characteristics of the radiation therapy system, wherein the multiple characteristics comprise possible leaf positions defining possible apertures of the MLC and possible radiation fluence values that are providable by the radiation therapy system;
   providing one or more planning objectives, wherein the one or more planning objectives are indicative of a desired therapeutic radiation dose distribution that should be provided to the patient;
   providing an optimization function being indicative of a deviation of a radiation dose distribution from the one or more planning objectives, wherein the radiation dose distribution depends on a sequence of possible apertures defined by the possible leaf positions and the possible radiation fluence values, and wherein the optimization function is further indicative of an uncertainty of the radiation dose distribution at edges of the possible apertures; and
   determining an optimized therapy plan by determining a sequence of possible apertures and possible radiation fluence values for which the optimization function is optimized, wherein the sequence of optimized possible apertures and optimized possible radiation fluence values defines the optimized therapy plan.

18. A non-transitory computer-readable medium with instructions stored thereon for determining a radiation therapy plan for a radiation therapy system comprising a multi-leaf collimator (MLC) comprising a plurality of movable leaves for shaping an aperture of the MLC such that a radiation beam is shaped by the aperture before being provided to a patient, wherein the instructions cause the radiation therapy system to:
- provide multiple characteristics of the radiation therapy system, wherein the multiple characteristics comprise possible leaf positions defining possible apertures of the MLC and possible radiation fluence values that are providable by the radiation therapy system;
- provide one or more planning objectives, wherein the one or more planning objectives are indicative of a desired therapeutic radiation dose distribution that should be provided to the patient;
- provide an optimization function being indicative of a deviation of a radiation dose distribution from the one or more planning objectives, wherein the radiation dose distribution depends on a sequence of possible apertures defined by the possible leaf positions and the possible radiation fluence values, and wherein the optimization function is further indicative of an uncertainty of the radiation dose distribution at edges of the possible apertures; and
- determine an optimized therapy plan by determining a sequence of possible apertures and possible radiation fluence values for which the optimization function is optimized, wherein the sequence of optimized possible apertures and optimized possible radiation fluence values defines the optimized therapy plan.

19. The non-transitory computer-readable medium of claim 18, wherein the radiation therapy system is adapted to continuously change between possible beam directions, leaf positions and radiation fluence values while generating the radiation beam, wherein the uncertainty for a radiation dose distribution resulting from a sequence of continuously changing possible beam directions, leaf positions and radiation fluence values is estimated based on summing over uncertainties determined for partial radiation dose distributions determined for a plurality of directions of the sequence of continuously changing possible beam directions.

20. The non-transitory computer-readable medium of claim 18, wherein the uncertainty for a radiation dose distribution is modeled based on an uncertainty function centered at, at least one edge of each possible aperture, wherein the uncertainty function of a respective edge comprises a width corresponding to an anticipated uncertainty for the respective edge, and wherein the uncertainty function of each edge of the at least one edge of each possible aperture is weighted with a possible fluence value that is associated with the possible aperture to which the respective edge belongs.

* * * * *